United States Patent [19]

Zamore

[11] Patent Number: 4,590,214
[45] Date of Patent: May 20, 1986

[54] METHOD OF TREATMENT FOR HERPES

[75] Inventor: Leonard Zamore, Woodbridge, Conn.

[73] Assignee: Sepreh, Inc., Woodbridge, Conn.

[21] Appl. No.: 277,174

[22] Filed: Jun. 25, 1981

Related U.S. Application Data

[63] Continuation of Ser. No. 139,842, Apr. 14, 1980, abandoned.

[51] Int. Cl.⁴ ..................... A61K 31/11; A61K 33/00; A61K 33/04
[52] U.S. Cl. ..................... 514/702; 514/705; 514/934; 424/127; 424/164
[58] Field of Search ....................... 424/333, 127, 164; 514/702, 705

[56] References Cited

U.S. PATENT DOCUMENTS 3,016,328  1/1962  Pepper .................................. 424/333

Primary Examiner—Jerome D. Goldberg
Attorney, Agent, or Firm—Fishman & Dionne

[57] ABSTRACT

A method for treating and curing the viral disease of Herpes simplex is presented wherein a chemical composition comprising a saturated dialdehyde containing 2–6 carbon atoms, a lower alkanol and an alkalinating agent is applied directly to the erupted or broken blister or applied directly to the resulting ulcer at its initial stage of development.

7 Claims, No Drawings

METHOD OF TREATMENT FOR HERPES

This is a continuation of application Ser. No. 139,842, filed Apr. 14, 1980, now abandoned.

BACKGROUND OF THE INVENTION

The invention relates to a method of treating and curing Herpes simplex, an acute inflammatory virus disease of the skin or mucus membranes characterized by the eruption of small blisters on the skin and mucus membranes. More particularly, this invention relates to the treatment and cure of Herpes by application of a chemical composition broadly comprised of a mixture of a saturated dialdehyde, a lower alkanol containing from 1 to 3 carbon atoms and a alkalinating agent to the erupted to broken blisters or the newly formed ulcers.

While the prior art discloses no known cure for the viral disease Herpes simplex, the various chemical compositions used in the present invention are disclosed in U.S. Pat. No. 3,016,328. The only disclosed and known use of these chemical compositions is for in vitro disinfecting medical and surgical instruments and household objects. However, this in vitro evidence for cidal action for a chemical does not make the use of the chemical for in vivo applications obvious to a person of ordinary skill in the art. In vivo utility can only be determined by careful clinical trials using double-blind, perspective randomized placebo-controlled cross-over studies. These studies are essential to determine the effect upon the in vivo use of the chemical compositions from such factors as metabolism, chemical transport, and other inhibiting and antagonistic local events. Thus, the known in vitro use, for the chemical does not establish that the same chemical composition may be used in vivo.

SUMMARY OF THE INVENTION

The present invention discloses a method of curing the viral disease Herpes simplex by the application of a chemical solution broadly comprised of a saturated dialdehyde, lower alkanol containing from 1 to 3 carbons and an alkalinating agent to the infected mucus area.

The method in accordance with the preferred embodiment of the present invention requires the application of a prepared solution of the above components to the blister at the time it erupts or breaks, or to the ulcer at its initial stage of formation. Application of the solution at other times is not totally effective.

DESCRIPTION OF THE PREFERRED EMBODIMENT

The onset of an acute attack of Herpes simplex starts with a redness and swelling of a localized area of the skin or a mucus membrane. This inflammation proceeds to form a blister. This blister then breaks forming an ulcer which eventually dries to form a scab. Within 7 to 14 days and signs and symptoms of the disease disappear.

A solution of a saturated dialdehyde, a lower alkanol containing from 1 to 3 carbon atoms and an alkalinating agent is prepared according to any of the disclosed embodiments from U.S. Pat. No. 3,016,328. In a preferred embodiment of the present invention, the user is provided a multi-sectioned package containing proper proportions of the dialdehyde and alkaline components with directions for the admixture with the required volume of the solvent system; for example aqueous-alkanolic solution. This solution is then applied to the affected lesion in the vesicle stage at the moment the blister erupts or is broken, or it is applied to the ulcer at its initial stage. The solution is applied two times daily until a scab forms. If the solution is not applied at the correct time it has been determined that the result will be only a partial remission of the disease or a more rapid subsiding of the symptoms.

It is theorized that the Herpes virus travels along the course of a specific nerve which communicates the spinal column to the skin or mucus membrane. It is believed that the virus is activated when the body is put under stress. The viral particles then travel along the course of the nerve to the skin or mucus membrane and cause the formation of a blister. Once the blister erupts or is broken the virus travels back along the course of the same nerve to the spinal column and remains dormant until activated again. This would account for the incomplete curing of the disease if the treatment is postponed for too long a period of time after the blister erupts or is broken. It is emphasized that the above is only a theory, which has not been fully established, and should not be taken in any fashion to limit the scope of the present invention.

While a preferred embodiment has been shown and described, various modifications and substitutions may be made thereto without departing from the spirit and scope of the invention. Accordingly, it will be understood that the present invention has been described by illustration and not limitation.

What is claimed is:

1. A method of treating the viral disease Herpes in a living body which comprises the step of subjecting an inflamed area of the body to a treatment with a composition comprising a saturated dialdehyde containing from 2 to 6 carbon atoms, a lower alkanol and an alkalinating agent.

2. The method of claim 1 including the step of applying said composition to one or more erupted or broken blisters in the inflamed area or to one or more newly formed ulcers.

3. The method of claim 1 wherein the alkalinating agent is an alkali metal salt selected from the group consisting of carbonates, bicarbonates and mixtures thereof.

4. The method of claim 1 wherein the alkalinating agent is a member of the group consisting of dialkylaminoalkanol, trialkylamine and dialkylamine.

5. The method of claim 1 including the steps of supplying the composition in separated portions of dialdehyde and alkaline components in one portion and solvent system in another portion, and mixing said separated portions to form an activated solution for use.

6. The method of claim 5 wherein the solvent system is an aqueous-alkanolic solution.

7. The method of claim 5 wherein the solvent system is an aqueous solution.

* * * * *